United States Patent [19]

Revici

[11] Patent Number: 4,609,552

[45] Date of Patent: Sep. 2, 1986

[54] METHOD FOR TERMINATING PREGNANCY

[75] Inventor: Emanuel Revici, New York, N.Y.

[73] Assignee: Elena Avram, New York, N.Y.

[21] Appl. No.: 722,900

[22] Filed: Apr. 12, 1985

Related U.S. Application Data

[63] Continuation-in-part of Ser. No. 487,900, Apr. 22, 1983, abandoned.

[51] Int. Cl.⁴ ............................................. A61K 33/04
[52] U.S. Cl. ................................ 424/164; 424/195.1; 514/549; 514/560; 514/706
[58] Field of Search ...................... 514/549, 560, 706; 424/164, 165

[56] References Cited

U.S. PATENT DOCUMENTS 4,368,206  1/1983  Revici .................................. 424/312

Primary Examiner—Leonard Schenkman
Attorney, Agent, or Firm—Pennie & Edmonds

[57] ABSTRACT

A method for terminating pregnancy which comprises internally administering to the body a sufficient amount of a bivalent negative sulfur composition to induce menstruation.

6 Claims, No Drawings

METHOD FOR TERMINATING PREGNANCY

CROSS-REFERENCE TO RELATED APPLICATIONS

This application is a continuation-in-part of application Ser. No. 487,900, filed Apr. 22, 1983 now abandoned.

TECHNICAL FIELD

This invention relates to a method for terminating pregnancy by administering to the body an amount of elemental sulfur or a non-toxic bivalent negative sulfur composition sufficient to terminate the pregnancy by inducing menstruation.

DETAILED DESCRIPTION OF THE INVENTION

Examples of non-toxic bivalent negative sulfur compositions that can be used according to the invention include the reaction products of allylic unsaturated fatty acids or esters and sulfur. As disclosed in U.S. Pat. No. 4,368,206, such reaction products are produced by oxidizing a liquid composition containing a fatty acid or fatty ester, structurally characterized by allylic unsaturation, for example, by bubbling air through the reaction mixture. The fatty acid or ester advantageously includes elemental sulfur and/or a conventional free radical initiator such as tertiary-butyl peroxide during the heating step.

The allylically unsaturated compound is preferably a naturally occurring oil containing polyunsatuarated fatty esters, such as an animal, vegetable, or fish oil, and, particularly, polyunsaturated vegetable oils. Sesame oil, a vegetable oil consisting largely of triglycerides, is the most advantageous composition found to date in the practice of this invention.

The composition utilized should contain a significant percentage of molecular species having allylic moieties to render the compositions useful according to the invention. Such moieties are indicated by the following partial structures —CH=CH—CH$_2$—CH=CH— and/or —CH=CH—CH=CH—CH$_2$. As indicated, the unsaturation can be conjugated or nonconjugated, but the composition must contain allylic methylene hydrogen.

Such compositions should be oxidized or heated in the presence of oxygen at a temperature range between about 110° C. and about 150° C. The oxygen can be obtained by merely heating the composition in a vessel which is open to the atmosphere, but preferably and advantageously, the source of oxygen is a gas such as air which is injected into the heated oil. Introduction of air also provides a source of agitation.

As previously stated, it is most advantageous to add elemental sulfur such as sublimed, precipitated, or washed sulfur to the compositions so that the sulfur is present with oxygen during at least a portion of the heating period and the sulfur becomes incorporated into the composition. Additionally, a previous batch of the oxidized oil with or without sulfur or any commonly known and available free radical initiator, such as terbutyl peroxide, may advantageously be present during at least a portion of the heating period.

If sulfur is added to the selected composition, for example, sesame oil, the temperature should be maintained at an upper limit within the range of about 120° C. to about 130° C., and preferably about 125° C. to 127° C. These temperature limitations are based on a heating time of about one-half hour. The temperatures can be altered within limits depending on the time of heating. For example, the temperature can be 129°–130° C. if the time is shorter, or at temperatures as high as 150° C. for brief periods of time. High temperatures for a prolonged period of time tend to degrade the composition and should thus be avoided.

If sulfur is not present during the heating period, the temperature should be maintained in the range between about 110° C. and about 150° C. and preferably in the range between about 120° C. and about 140° C.

The heat treatment is conducted for a period of from about 15 minutes to about two hours. If sulfur is present, optimal results are obtained if the heat treatment is conducted for a period of time between about 30 minutes and about 1 hour. If a free radical initiator is present, or if a selected composition inherently contains a significant amount of initiator, the heat treatment period may be conducted for a much shorter period of time.

The precise nature of the compositions which result from the above-described treatment or the identity of the effective component or components is not presently known. Also, it appears that a correlation exists between a composition useful for the purpose of the invnetion and its presumed peroxide or hydroperoxide content. By adhering to the process according to this invention, it has been found that efficacious compositions are produced which yield a significant peroxide titer when monitored by conventional iodometric analysis, the results being expressed for example, in terms of microequivalents per gram or milliequivalents per kilogram. By significant peroxide titer is meant a value obtained which is greater than that which inherently may be present in the initial untreated compound.

In the case of triglycerides which contain the allylic type unsaturation as described above, the resulting oxidized species is thought to be a hydroperoxide represented by the following partial structure

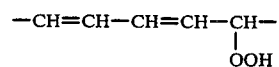

as interpreted via UV spectroscopic analysis, inter alia.

Whatever the nature of the oxidized species (with or without the addition of sulfur), it appears amenable to monitoring by conventional iodometric analysis.

Although it appears that the activity of the composition is coincident with the presence of peroxides or hydroperoxides, the efficacious agent need not necessarily be directly derived from these classes. It may be in fact be those species derived from radicals resulting from decomposition of compounds of this class and may involve reaction with other molecules of, for example, triglyceride oils or sulfur including olefinic polymerization products and/or lower molecular weight decomposition products of the oils or additional products with sulfur such as sulfides, disulfides, hydropersulfides, etc.

With regard to a preferred embodiment, it appears that the presence of elemental sulfur (approximately 1% by weight based on sesame seed oil) during the oxidation of sesame seed oil acts to increase the amounts of oxidation products (conjugated hydroperoxides, diene, triene, unsaturated carbonyl) and that this increase appears optimal near 127° C. as evidenced by UV spectroscopic analysis studies. In the absence of sulfur, it appears that the region near 137° C. is optimal for the production of oxidation products.

As mentioned above, it appears that the most effective compositions are those which have a relatively high peroxide titer. Such trend of effectiveness agrees in general with the results of a peroxide analysis involving the above-identified oils in their untreated state and when oxidized in the presence of elemental sulfur under similar conditions as shown in Table I.

It is believed that the lower peroxide titer of cottonseed oil is due to the presence of natural antioxidants. The elimination of the anti-oxidants from oils such as corn and cottonseed oil or the use of the relatively pure allylically unsaturated compounds or mixtures thereof will result in a substantially increased peroxide titer when treated according to this invention.

TABLE I

PEROXIDE ANALYSIS (meq/kg)

| Oil Used (Peroxide Analysis) | "A" Oil Saturated With Sulfur | "B" Oil Treated* With Sulfur and Air | Δ = "B − A" Difference In Peroxide |
|---|---|---|---|
| Sesame Seed (10.2) | 18.8 | 35.7 | 16.9 |
| Corn (6.8) | 11.3 | 14.9 | 3.6 |
| Cottonseed (7.3) | 10.9 | 10.2 | −0.7** |
| Olive (5.9) | 12.4 | 13.8 | 1.4 |
| Triolein (7.2) | 8.6 | 8.5 | −0.1** |

*Heated at 127° C. for 0.5 hrs with 90 1/min air addition and rapid mechanical stirring and containing 1.0% elemental sulfur by weight.
**Within experimental error.

Triolein contains only oleic acid moieties which are characterized by the allylically unsaturated group —CH=CH—CH$_2$—and hence is quite difficult to oxidize, * particularly when compared to the preferred sesame seed oil or other polyunsaturated oils. A peroxide titer value of 35.7 meq/kg has been attained for the sesame seed oil-sulfur-oxygen treated composition whle sesame seed oil oxidized alone at 137° C. yields a value of 63.3 meq/kg.
J. Sci. Fd. Agric. 1975, 26, 1353-1356. A peroxide titer value of 35.7 meq/kg [Δ=(35.7−18.8)=16.9] has been attained for the sesame seed oil-sulfur-oxygen treated composition while sesame seed oil without sulfur oxidized at 137° C. yields a value of 63.3 meq/kg [Δ=(63.3−10.2)=53.1].

Generally a substantial increase in the peroxide titer value can be defined as Δ3 to about Δ100 in cases where sulfur is incorporated into the composition and as from about Δ3 to about Δ400 when the oil is oxidized alone, or in the absence of sulfur.

The process used for determining the peroxide titer values discussed and reported herein are determined by placing a 2 gram sample of the composition in a flask purged with nitrogen, and adding thereto 2 ml of concentrated acetic acid and 0.5 grams of potassium iodide. The mixture is capped to exclude air and allowed to remain in the dark for 30 minutes to complete the reaction. The side walls are then wet with a minimum amount of water and approximately 1-2 ml of a 2% starch added thereto. The solution is then immediately titrated to the end point with 0.007 normal Na$_2$S$_2$O$_3$ solution. The end point is white when small amounts of peroxides are present and slightly yellow when larger amounts are present.

The compositions as prepared according to the process of this invention should be used relatively soon after preparation as there is indication that the peroxide titer values and effectiveness of the compositions decrease upon aging.

Preferred compositions according to this invention can be prepared by adding the sulfur to the oil, such as sesame oil, and heating the mixture with agitation at a temperatures of about 130° C. For clear solutions, the mixture can be heated between about 120° C. and 127° C. Heating the mixture above about 130° C. for a sufficient time causes a progressive color change in the mixture which otherwise does not appear to be detrimental. The temperatures given above relate to the use of sulfur with sesame oil. Ranges of temperatures which can be used to produce the compositions made according to this invention may vary with the particular oil being used, but generally temperatures between about 120° C. and 150° C. are sufficient for most oils when sulfur is added.

It is preferred to heat the oil and sulfur at about 150° C. for 15 minutes to a half hour or until the compositions turn to a fairly deep black color. The oil used, together with sublimed or precipitated sulfur, is preferably rich in conjugated and polyunsaturated acids, such as safflower, corn, cod liver, sardine, salmon or tung oil or an oil extract from Bixa orellana seeds. The polunsaturated fatty acids can be treated with 50% KOH before incorporation of the sulfur therein. The oils having the sulfur incorporated therein and the crystals which are separated therefrom after cooling can be administered separately but preferably together. These compositions heated to about 150° C. are presently preferable.

If the oil and sulfur is heated below about 90° C., it is difficult to incorporate the sulfur into the oil by heating and stirring alone. The best results have been obtained to date by maintaining the temperature used in forming the compositions over a prolonged period of time from about 30 minutes to one hour. Stirring aids in the reaction, and experiments to date indicate that a fairly violent stirring is advantageous. The introduction of air into the mixture during the heating is also very advantageous, particularly when the mixture is not subjected to prolonged heating and thus, is the preferred method. The mixing or stirring can be accomplished with the introduction of the air.

After the reaction has taken place, the mixture is cooled. The remaining fluid is ready for use after appropriate sterilization for injection or incorporated into capsules, such as gelatin, for oral administration. As mentioned above the sulfur crystals remaining in the bottom of the reaction vessel may also be used with or without the oil.

The amount of sulfur incorporated into the oil is advantageously between about 0.1% to 2.5% by weight, based on the oil. If higher amounts of sulfur are used, it will generally precipitate. There appears to be no advantage to using higher amounts of sulfur in any event since the ultimate dosage given to the patient is the criterion, rather than the amount of sulfur content in the oil.

As can be observed from Example 2 below, the incorporation of the sulfur into the oil also seems to be limited to about 1% by the process presently described and utilized for producing these sulfurized unsaturated oils.

The sulfur content can be much less than about 1% if desired and smaller sulfur content is advantageous when administered by injection. Varying the amount of sulfur below about 1% incorporated in the polyunsaturated oils for oral administration only affects the number of capsules to be taken at a given time by a particular patient.

Experiments to date indicate that the optimum sulfur content for oral administrations is about 1% and by injection about 0.1% to 0.3% by weight of the sulfur based on the weight of the oil.

Further examples of non-toxic bivalent negative sulfur compounds that can be used include thiosulfates, thiosinamine, thio or thiol compounds, such as thioacids and their non-toxic salts or esters, thioglycerol, thioglycol, thiopropanediol, dithiopropanol, ethyl sulfide and ethylene sulfide. Colloidal sulfur can also be used. Colloidal sulfur has been found to form sulfides in the intestines.

The invention also includes the use of selenium in place of elemental sulfur and for the same use. When using selenium it is combined with the allylic moiety in the same manner as sulfur but heated to a temperature in the range of 230° to 250° C., preferably about 240° C. from 15 minutes to an hour or more until the peroxide titer value is substantially greater than that of the untreated allylic moiety in the same manner as disclosed herein with respect to the use of sulfur. These compositions into which selenium is incorporated have to date not indicated as good an effect as those compositions into which sulfur is incorporated.

The amount of bivalent negative sulfur compound that is administered to terminate the pregnancy by including a menstruation period will, of course, vary depending upon the particular compound being employed, since the activity of the sulfur and percentage found therein will be somewhat variable. The body weight is also a factor as is well known in the art. Generally, for the average size human, a dose of about 1 gram 3 to 5 times a day is sufficient to terminate the pregnancy by inducing menstruation. Therapy can be continued from day to day until menstruation reappears. Usually this occurs within 1 to 2 days of treatment.

The inducement of the menstruation and the corresponding termination of the pregnancy is effected by a catabolic local process, with a lytic action upon the uterine mucuous membrane. The administration of these compounds causes predirectly uterine catabolic changes which restores the menstruation.

The invention is useful for the treatment of lower animals as well as humans.

The compositions are preferably administered orally, but can be administered by injection, as suppositories or even vaginally.

An advantageous oral dose has been found to be about 20 drops in a gelatine capsule. Patients are generally advised to take one capsule twice a day, for two days after which menstruation should begin.

When the sulfurized oil is used by injection, such as intramuscularly or intraperitoneally, it is advantageous to have the sulfur contained in the sulfurized oil below about 0.5% by weight, preferably between about 0.1% to 0.3% by weight, and to inject ½ to 3 ml of this solution into the patient. Experiments to date indicate that the injection of sulfurized oil is somewhat painful when it contains above about 0.5% sulfur. Administration by injection is, of course, not necessary but it may act faster initially. Generally if a person is given the initial injection of the sulfurized oil, he can also be given a supply of the oral capsules and directed to take 3 to 4 capsules a day following the injection for one week.

EXAMPLE 1

A sulfurized oil was prepared by mixing 50 grams of sublimed sulfur, obtained from Fisher Scientific, with one liter of sesame oil. The mixture was heated under fairly rapid agitation by air to a temperature of about 127° C. until all of the sulfur was incorporated into the sesame oil. The reaction mixture was then cooled to room temperature, producing at the bottom of the reaction vessel a small amount of sulfur crystals. The crystals were then separated from the liquid by filtration and about half of the crystals replaced in the resulting liquid, wherein they slowly dissolved.

The resulting sulfurized oil was then incorporated into gelatin capsules in the amount of (about 20 drops) per capsule.

EXAMPLE 2

For women of average size, these recommended dosage of such capsules is one capsules, twice a day for 2 days, and this has been found sufficient in most cases to induce menstruation and terminate the pregnancy. One skilled in the art would be able to vary the dosage according to the size of the person to be treated; 4 g. of sulfur were weighed out and placed in an Erlenmeyer flask. 200 ml of sesame oil were added; the contents were heated to 125° C. with stirring until the sulfur dissolved. The flask was removed from heat and allowed to cool to room temperature (5 hours). Sulfur crystals were filtered into a Buchner funnel, washed thoroughly with hexane to remove residual oil, and weighed.

The above example was repeated three times. The washed sulfur precipitate was weighed in each trial and the amount of sulfur in the sesame oil calculated by difference as follows:

Initial weight of sulfur: 4.00 g
Weight of sulfur ppt.:
Trial 1 2.05 g
Trial 2 2.00 g
Trial 3 1.92 g
% (w/v) sulfur in sesame oil:
Trial 1 1.02%
Trial 2 1.00%
Trial 3 0.96%
Average 0.99%

From this it was concluded that the solutions contained approximately 1% sulfur after filtration. These formulations were substituted into the capsules of Example 1 and were found to produce similar results.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

I claim:

1. A method for terminating a pregnancy in a body which comprises internally administering to the body a reaction product produced by heating an oil containing at least one fatty acid or fatty ester having an allylic unsaturation of the type —CH=CH—CH$_2$—CH=CH— —and/or —CH=CH—CH=CH—CH$_2$- and thiopropanediol, dithiopropanediol, dithiopropanol, ethyl sulfide, ethylene sulfide or colloidal sulfur at a temperature above about 110° C. for a sufficient period time to incorporate at least 0.1% of sulfur into the allylically unsaturated oil.

2. A method for terminating a pregnancy in a body which comprises internally administering to the body a reaction product produced by heating an oil containing at least one fatty acid or fatty ester having an allylic unsaturation of the type —CH=CH—CH$_2$—CH=CH— and/or —CH=CH—CH=CH—CH$_2$- and elemental sulfur at a temperature above about 110° C. for a sufficient period of time to incorporate at least 0.1% of sulfur into the allylically unsaturated oil.

3. The method of claim 2 in which the sulfur and oil composition is heated to a temperature and for a period of time to render the composition substantially black in color.

4. The method of claim 3 in which 20 drops of the composition in a gelatine capsule is administered orally to a body twice a day for two days.

5. A method for terminating a pregnancy in a body which comprises internally administering to the body a reaction product produced by heating an oil containing at least one fatty acid or fatty ester having an allylic unsaturation of the type —CH=CH—CH$_2$—CH=CH— and/or —CH=CH—CH=CH—CH$_2$—and selenium at a temperature between about 230° and 250° C. for a sufficient time to incorporate at least 0.1% of selenium into the allylically unsaturated oil.

6. The method of claim 5 in which 20 drops of the composition in a gelatine capsule is administered orally to a body twice a day for two days.

* * * * *